US009101532B2

(12) United States Patent
Hiranuma

(10) Patent No.: US 9,101,532 B2
(45) Date of Patent: Aug. 11, 2015

(54) MEDICINE STORAGE CONTAINER

(71) Applicant: TERUMO KABUSHIKI KAISHA, Shibuya-ku (JP)

(72) Inventor: Takaaki Hiranuma, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/958,300

(22) Filed: Aug. 2, 2013

(65) Prior Publication Data

US 2013/0313215 A1 Nov. 28, 2013

Related U.S. Application Data

(63) Continuation of application No. PCT/JP2012/052394, filed on Feb. 2, 2012.

(30) Foreign Application Priority Data

Feb. 4, 2011 (JP) ................................ 2011-022334

(51) Int. Cl.
*A61B 19/00* (2006.01)
*A61J 1/14* (2006.01)
*A61J 1/05* (2006.01)
*A61J 1/20* (2006.01)

(52) U.S. Cl.
CPC .... *A61J 1/14* (2013.01); *A61J 1/05* (2013.01); *A61J 1/1406* (2013.01); *A61J 1/2093* (2013.01); *A61J 1/2096* (2013.01); *A61J 2001/201* (2013.01)

(58) Field of Classification Search
CPC .... B65D 21/006; B65D 81/264; B65D 1/267; B65D 83/32
USPC ............... 215/6; 206/438, 219, 222; 604/410, 604/403, 416
See application file for complete search history.

(56) References Cited

U.S. PATENT DOCUMENTS 4,645,073 A * 2/1987 Homan ......................... 206/219
5,437,381 A * 8/1995 Herrmann .................... 215/11.1

(Continued)

FOREIGN PATENT DOCUMENTS

JP 49-27388 A 3/1974
JP 2000-508993 A 7/2000

(Continued)

OTHER PUBLICATIONS

International Search Report (PCT/ISA/210) issued on Apr. 17, 2012, by the Japanese Patent Office as the International Searching Authority for International Application No. PCT/JP2012/052394.

*Primary Examiner* — Anthony Stashick
*Assistant Examiner* — Raven Collins
(74) *Attorney, Agent, or Firm* — Buchanan Ingersoll & Rooney PC

(57) ABSTRACT

A liquid medicine storage container has a container body and a medicine stored in the container body. The container body includes a first space provided on the distal end, into which a liquid is injected, a second space provided more to the proximal end than the first space, for storing the medicine, and at least one guide passage that communicates the first space and the second space and that guides a liquid injected from the first space to an inner surface of the second space. The container body is configured so that the liquid guided to the inner surface is supplied to the medicine by flowing along the inner surface. A plurality of guide passages is arranged with intervals therebetween along a circumferential direction of the container body.

20 Claims, 8 Drawing Sheets

(56) References Cited

U.S. PATENT DOCUMENTS

| | | | | |
|---|---|---|---|---|
| 6,041,969 | A * | 3/2000 | Parise | 222/129 |
| 6,378,714 | B1 * | 4/2002 | Jansen et al. | 215/249 |
| 2008/0255535 | A1 * | 10/2008 | Yoshikawa | 604/410 |

FOREIGN PATENT DOCUMENTS

| | | | |
|---|---|---|---|
| JP | 2001-258991 | A | 9/2001 |
| JP | 2006-055452 | A | 3/2006 |
| WO | WO 97/39952 | A1 | 10/1997 |

* cited by examiner

MEDICINE STORAGE CONTAINER

CROSS REFERENCES TO RELATED APPLICATIONS

This application is a continuation of International Application No. PCT/JP2012/052394 filed on Feb. 2, 2012, claims priority to Japanese Application No. 2011-022334 filed on Feb. 4, 2011, the entire content of both of which is incorporated herein by reference.

TECHNICAL FIELD

The present invention generally relates to a medicine storage container.

BACKGROUND DISCUSSION

Normally, medicines are stored in a vial container (medicine storage container) sealed off with a rubber stopper. An example is disclosed in Japanese Patent Laid-Open No. 2006-55452.

In the case of taking out a medicine that is in, for example, powdery form from such a vial container, an injection needle is attached to a distal end of a syringe with a dissolving liquid stored therein, then the injection needle is made to pierce through the rubber stopper of the vial container, and the dissolving liquid is injected into the vial container. As a result, a dissolving liquid with the medicine dissolved ion the liquid (hereinafter referred to as "liquid medicine") is obtained. In the case of such a vial container, however, there would be the following problems. The dissolving liquid flowing out of the injection needle would directly drip onto the medicine with vigor, resulting in foaming of the liquid medicine (generation of bubbles in the liquid medicine). Consequently, in sucking the liquid medicine out of the vial container by use of an injection needle or the like, accurate metering may be impossible, or the liquid medicine may be nonuniform in concentration.

SUMMARY

According to one aspect disclosed here, a medicine storage container comprises: a container body possessing a distal end and a proximal end, and in which a medicine is stored; the container body including a first space on a side of the distal end and having an opening through which a liquid is injected, a second space storing the medicine, the second space provided closer to a side of the proximal end than the first space and possessing an inner surface; a partition part spatially partitioning the first space and the second space; the partition part including at least one guide passage communicating the first space and the second space and guiding the liquid injected through the opening into the first space to the inner surface of the second space.

The medicine storage container is well suited to restraining foaming of a liquid medicine.

The guide passage can be configured so that the liquid guided to the inner surface is supplied to the medicine stored in the second space by flowing along the inner surface.

The at least the one guide passage can be in the form of a plurality of guide passages, with the plurality of guide passages being provided at intervals along a circumferential direction of the container body.

The guide passage can be sector-shaped in a plan view of the container body as viewed from the side of the distal end.

The second space can be configured to have a gradually decrease inside diameter zone having an inside diameter gradually decreasing along a direction toward the side of the proximal end, wherein the liquid is supplied to the medicine while flowing along an inner surface of the gradually decreasing inside diameter zone.

The partition part can be configured to include a projected part projected toward an inside of the second space, with the projected part having an inclined surface inwardly inclined toward the side of the proximal end of the container body, and an opening on a side of the second space of the guide passage is formed at a circumferential edge of the projected part.

The container body can has a structure in which a first member constituting the first space and the partition part and a second member constituting the second space are joined to each other.

The medicine storage container can also have a valve or a cap capable of being pierced through by a needle body, and the valve or the cap is provided at the opening, whereby the container body is sealed in a gas-tight manner.

According to another aspect, a medicine storage container comprises: a hollow container body possessing a distal end and a proximal end; with the container body including a partition part, a first space and a second space; and wherein the second space is located on a side of the partition part opposite the first space and is located closer toward the proximal end of the hollow container body than the first space, and wherein the second space containing medicine and possessing an inner surface surrounding the second space. The first space is located on a side of the partition part opposite the second space and is located closer toward the distal end of the hollow container body than the second space, with the first space having an opening through which liquid is injected to be mixed with the medicine in the second space; the partition part spatially partitions the first space from the second space, and the partition part includes at least one guide passage having opposite open ends opening into the first space and the second space so that the first and second spaces are in fluid communication with one another through the at least one guide passage. The at least one guide passage is angled outwardly in a direction approaching the second space so that the liquid injected into the first space flows through the at least one guide passage and is guided toward the inner surface of the second space, enters the second space and flows down the inner surface of the second space. In addition, a valve or a cap is positioned so that the first space is located between the partition part and the valve or a cap.

DETAILED DESCRIPTION

A first embodiment of a medicine storage container according to the disclosure here will be described with reference to FIGS. 1 and 2. In the description which follows, for purposes of convenience, the upper side in each of FIGS. 1 and 2 is referred to as "upper", and the lower side in each of the figures as "lower".

Figure 1:
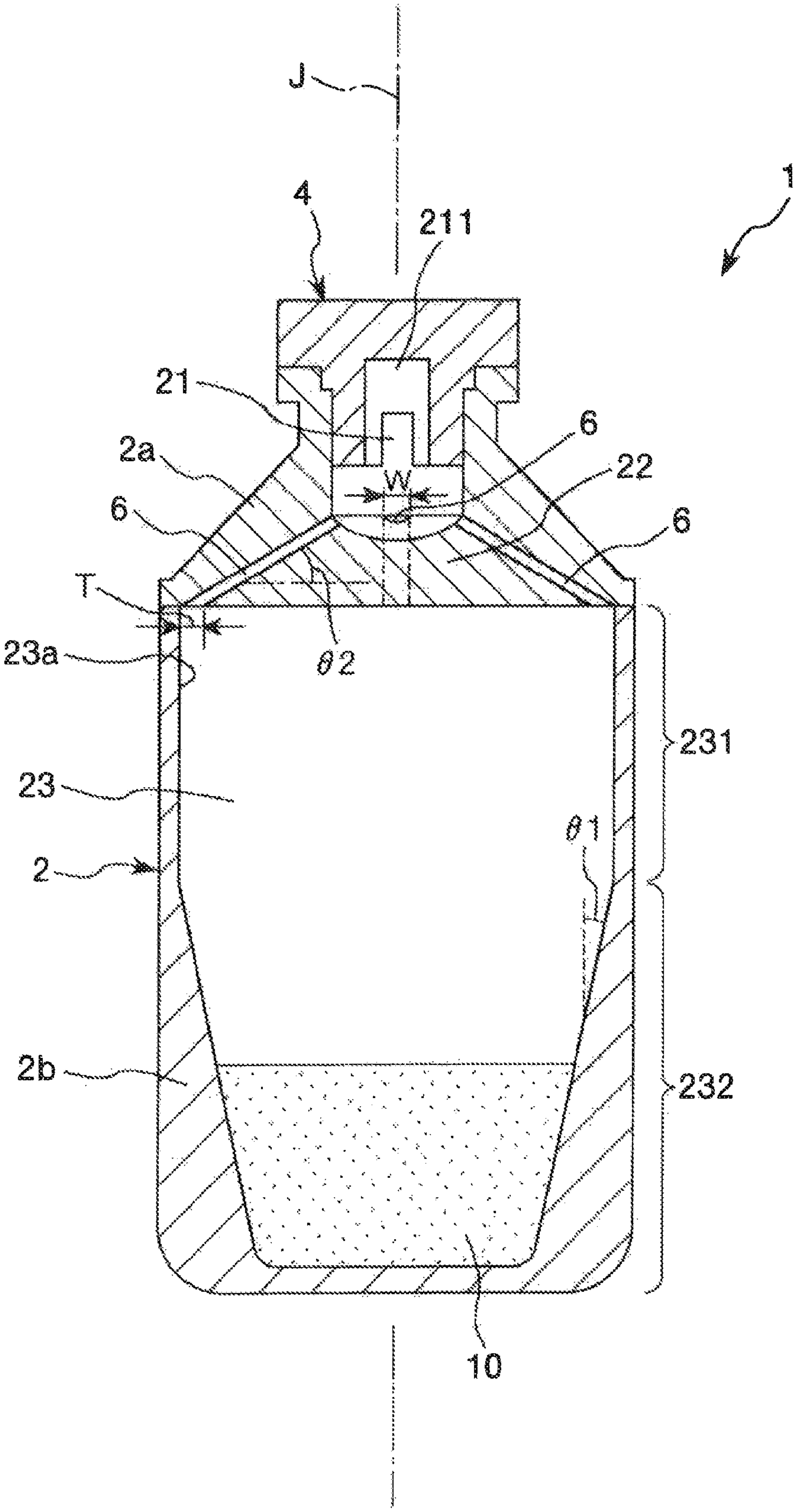
FIG. 1 is a longitudinal cross-sectional view showing a first embodiment of a medicine storage container disclosed here.
Figure 2:
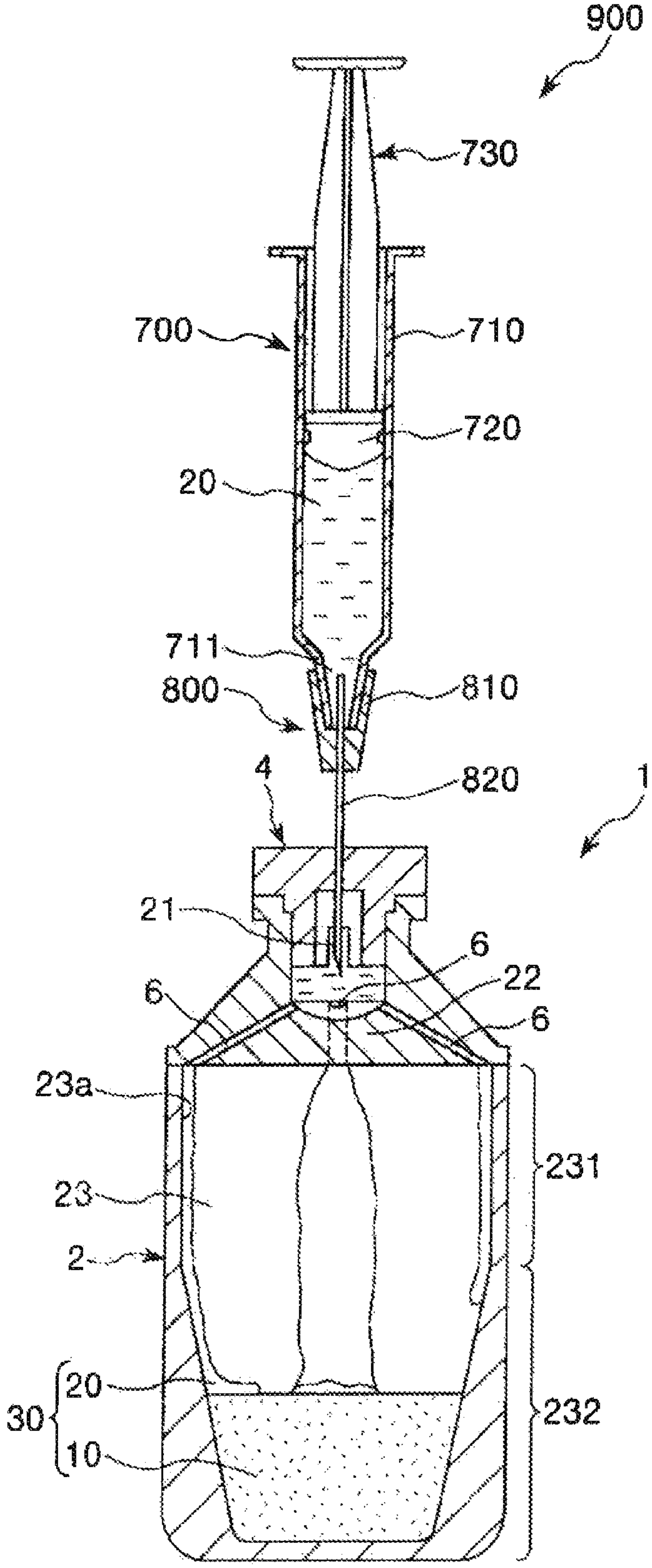
FIG. 2 is a cross-sectional view illustrating a method of using the medicine storage container shown in FIG. 1.

A medicine storage container (vial container) 1 shown in FIG. 1 includes a container body 2, and a medicine 10 stored in the container body 2. In addition, the medicine storage container 1 has a cap 4, by which gas-tightness of an inside of the container body 2 is maintained in the state before use (in custody).

In this medicine storage container 1, a liquid such as a dissolving liquid, a diluting liquid and a liquid medicine (such a liquid will hereinafter be referred to simply as the "liquid 20") is injected through a first space 21 into the container body 2, whereby an operation of mixing the medicine 10 with the liquid 20 or the like is conducted. In the following, a mixture of the medicine 10 and the liquid 20 will be referred to also as the "liquid medicine 30".

Examples of the medicine 10 stored in the container body 2 include solid preparations such as powdery preparations. In the case of the powdery preparations, sealing of the preparation can be carried out, for example, by subjecting the liquid medicine injected from the first space 21 into the container body 2 to freeze drying. Specific examples of the medicine 10 include vitamin preparations (vitamin complexes), various amino acids, antithrombogenic agents such as heparin, etc., protein preparations such as insulin, erythropoietin, a granulocyte colony-stimulating factor, growth hormone, a blood anticoagulant factor, etc., an antibiotic, an antinepplastic agent, an analgestic agent, a cardiac stimulant, an intravenous anesthetic, a drug for Parkinson's disease, a therapeutic agent for ulcer, an adenocortical hormone preparation, an antiarrhythmic, a correcting electrolyte, a protease inhibitor, and a thromboxane synthetase inhibitor, and the like.

As shown in FIG. 1, the container body 2 is in the shape of a bottomed hollow cylinder. The container body 2 includes: the first space 21 which is provided on an upper side (distal end) and has an opening 211; a second space 23 which is provided on a lower side (proximal end) and in which the medicine 10 is stored; and a partition part 22 by which the first space 21 and the second space 23 are spatially partitioned from each other.

The second space 23 includes: a constant diameter zone 231 of which inside diameter is substantially constant along an axial direction of the container body 2; and a gradually decreasing inside diameter zone 232 connected to a lower end of the constant diameter zone 231 and having an inside diameter that gradually decreases toward the lower end side. In the medicine storage container 1, the medicine (solid preparation) 10 is stored in the gradually decreasing inside diameter zone 232, and a free surface of the medicine 10 is located on the lower side of a boundary between the constant diameter zone 231 and the gradually decreasing inside diameter zone 232.

The height of the gradually decreasing inside diameter zone 232 is not particularly limited; preferably, it is about 0.7 to 1.3 times with respect to the height of the constant diameter zone 231. This helps ensure that the boundary between the constant diameter zone 231 and the gradually decreasing inside diameter zone 232 is located at a suitable position, and an effect as will be described later can be displayed more assuredly.

As will be described later, the medicine storage container 1 is so configured that the liquid 20 injected from the first space 21 is supplied to the medicine 10 by flowing along an inner surface **23*a* of the second space 23. With the gradually decreasing inside diameter zone 232 provided, a flow velocity of the liquid 20 immediately before being supplied to the medicine 10 can be suppressed. Therefore, the liquid 20 can be supplied to the medicine 10 more gently. It is also possible, for example, to lower the possibility of a situation in which the liquid 20 flowing along the inner surface 23*a* of the second space 23 parts or separates from the inner surface 23*a* before being supplied to the medicine 10, resulting in that drops of the liquid 20 fall directly onto the medicine 10**.

Here, an inclination angle θ1 of the inner surface **23*a* relative to the center axis J of the container body 2 in the gradually decreasing inside diameter zone 232 is not particularly limited; however, it is preferably about 5 to 20, more preferably about 10 to 15. This helps ensure that the above-mentioned effect is displayed effectively, and that an inside space of the gradually decreasing inside diameter zone 232, or a region to store the medicine 10**, can be secured sufficiently.

The first space 21 is shaped to be reduced in diameter, as compared with the second space 23. The first space 21 is formed with the opening 211 through which the inside and the outside of the container body 2 communicate with each other. Through this opening 211, the liquid 20 is injected into the container body 2.

In the present embodiment, the cap 4 composed of a rubber stopper, for example, is fitted in the first space 21, whereby the opening 211 is shut up. This helps ensure that the inside of the container body 2 is kept gas-tight.

The partition part 22 is provided between the first space 21 and the second space 23, to spatially partition these spaces from each other. Such a partition part 22 is roughly in the shape of a truncated cone, with its top face fronting the inside of the first space 21 and its bottom face fronting on the inside of the second space 23.

In addition, the partition part 22 is formed therein with guide passages 6 through which the first space 21 and the second space 23 communicate with each other. The guide passages 6 are through holes formed along the inclination of a side surface of the partition part 22. Each of the guide passages 6 has one end opening to the first space 21 and the other end opening to the second space 23. Such guide passages 6 have a function of guiding the liquid 20 injected from the first space 21 to the inner surface **23*a* of the second space 23. The liquid 20 guided to the inner surface 23*a* is supplied to the medicine 10 while flowing down the inner surface 23*a*** directly.

Since the guide passages 6 having such a function are thus provided, the liquid 20 can be supplied to the medicine 10 by flowing along the inner surface **23*a*, so that the supply of the liquid 20 to the medicine 10 takes place in a gentle manner. Therefore, the liquid medicine 30, which is the mixture of the medicine 10 and the liquid 20, can be restrained from foaming. Consequently, a liquid medicine 30 which can be metered accurately and which has the medicine 10 uniformly dissolved in the liquid 20** can be obtained.

Each of the guide passages 6 is so formed that a part of its opening fronting on the second space 23 is continuously connected to the inner surface **23*a* of the second space 23. In other words, the part of the opening fronting on the second space 23 is in contact with the inner surface 23***a* of the second space 23. This helps ensure that the liquid 20 having flowed in the guide passages 6 can be guided to the inner surface 23*a* more assuredly.

In the present embodiment, a plurality of the guide passages 6 is formed at regular intervals along a circumferential direction of the container body 2. This permits the liquid 20 to be relatively evenly guided to a plurality of parts of the inner surface 23*a* of the second space 23. Consequently, the liquid 20 can be supplied to the medicine 10 through a wider range, and smooth mixing of the liquid 20 with the medicine 10 can be achieved.

The number of the guide passages 6 is not particularly limited. Although the preferable number of the guide passages 6 varies depending on the size of the container body 2, a cross-sectional area of the guide passage 6 and the like factors, the preferable number is about 2 to 10. This helps ensure that the quantity of the liquid 20 guided to the second space 23 per unit time (the quantity will hereinafter be referred to simply as "guide quantity") can be set to an appropriate value, and the smooth mixing of the liquid 20 and the medicine 10 can be realized. It is also possible to effectively avoid a situation in which the guide quantity is too small so that it would take much time to mix the liquid 20 and the medicine 10. It is also possible to effectively obviate a situation in which the guide quantity is too large, so that the liquid 20 would be guided to the inner surface 23*a* of the second space 23 in a large quantity and that the flow velocity of the liquid 20 flowing down the inner surface 23*a* would be increased excessively.

In addition, an inclination angle 82 of each of the guide passages 6 relative to a plane to which the center axis J is orthogonal is not particularly limited; preferably, it is about 15 to 45, more preferably about 30 to 40, and further preferably about 33 to 36. This helps ensure that the flow velocity of the liquid 20 flowing inside the guide passages 6 will be a suitable velocity. Consequently, the liquid 20 can be efficiently guided to the inner surface 23*a*. The flow velocity of the liquid 20 flowing down the inner surface 23*a* can also be suppressed, so that the liquid 20 can be supplied to the medicine 10 in a gentle manner.

The cross-sectional area of each of the guide passages 6 is not particularly limited; preferably, it is about 1 to 50 mm2, more preferably about 5 to 20 mm2. This helps ensure that the guide quantity of the liquid 20 through each of the guide passages 6 can be brought to a suitable value.

The cross-sectional area of each guide passage 6 may be constant along an extending direction of the passage, or may vary along the extending direction. In the case where the cross-sectional area varies along the extending direction, it is preferable that the cross-sectional area is smaller on a downstream side than on an upstream side, for example, the cross-sectional area gradually decreases along the direction from the upstream side toward the downstream side. This helps ensure that the flow velocity of the liquid 20 on the downstream side in each guide passage 6 is suppressed, whereby the flow velocity of the liquid 20 flowing down the inner surface 23*a* of the second space 23 can be suppressed.

In addition, a cross-sectional shape of each guide passage 6 is not specifically restricted, and may be circular, tetragonal or the like; preferably, the cross-sectional shape is a flat shape (a shape flattened in the direction of the center axis J) with a width W greater than a depth L. Such a cross-sectional shape helps ensure that a wider region of the opening fronting on the second space 23 can be continuously connected to the inner surface 23*a* of the second space 23, so that the liquid 20 can be guided to the inner surface 23*a* more assuredly.

The height T of each guide passage 6 is not particularly limited; preferably, the height T is about 1 to 5 mm, more preferably about 2 to 3 mm. This enables the liquid 20 to flow within the guide passages 6 smoothly. Also, the liquid 20 can be guided to the inner surface 23*a* while keeping contact with an upper side of an inside surface of each guide passage 6. This surface portion is the surface continuous with the inner surface 23*a* of the second space 23. Therefore, when the liquid 20 flows down while in contact with the upper side of the inside surface of each guide passage 6, the liquid 20 can be guided to the inner surface 23*a* more assuredly. Though depending on a viscosity of the liquid 20 or the like factors, a configuration wherein the height of each guide passage 6 is less than 1 mm may cause the liquid 20 to be partly left in the guide passage 6. In such a situation, mixing of the liquid 20 and the medicine 10 may be incomplete. On the contrary, a configuration wherein the height of each guide passage 6 is in excess of 5 mm may cause the liquid 20 to come around. In such a case, the flow of the liquid 20 within the guide passage 6 may be disturbed, and smooth supply of the liquid 20 may be hampered.

In addition, the width W of each guide passage 6 may be constant along the extending direction, or may vary along the extending direction. In the case where the width W varies along the extending direction, it is preferable that, for example, the width on the downstream side gradually increases along the downstream direction, and a downstream portion of the guide passage 6 is formed in a tapered shape. With such a shape adopted, the liquid 20 having flowed through the guide passages 6 spreads in a wetting manner into a comparatively wide region in the circumferential direction of the inner surface 23*a* of the second space 23. Consequently, the flow velocity of the liquid 20 flowing down the inner surface 23*a* can be suppressed, and the liquid 20 can be supplied to the medicine 10 in a gentle manner. The liquid 20 can also be supplied to the medicine 10 from a wider range, so that the smooth mixing of the liquid 20 and the medicine 10 can be achieved.

Thus, the configuration of the container body 2 has been described in detail above.

The container body 2 as above is formed by joining two members. Specifically, the container body 2 includes a first member 2*a* constituting the first space 21 and the partition part 22, and a second member 2*b* constituting the second space 23, and is formed by joining these members.

With the container body 2 thus formed from two members, the partition part 22 can be relatively easily formed by, for example, injection molding or the like. The method for joining the first member 2*a* and the second member 2*b* is not specifically restricted; thus, various joining methods such as, for example, contact bonding, welding, or adhesion can be used.

The material(s) constituting the container body 2 (the first and second members 2*a*, 2*b*) is not specifically restricted. Examples of the material(s) which can be used include resin materials such as thermoplastic resins, for example, polyolefins such as polyethylene, polypropylene, poly4-methylpentene, COC (cyclic olefin copolymers), COP (cyclic olefin polymers), etc., polyesters such as polyethylene terephthalate, etc., and vinyl resins such as polyvinyl chloride, polyvinyl alcohol, etc., metallic materials such as aluminum, etc., and various glass materials. These materials can be used either singly or in combination of two or more of them.

Now, the method for using the medicine storage container 1 will be described below, based on FIG. 2, while taking as an example a case in which a medicine 10 is dissolved or dispersed by use of a liquid 20 which is a dissolving liquid.

[1] First, a syringe assembly 900 with the liquid 20 stored therein is prepared. The syringe assembly 900 has a syringe 700, and an injection needle 800 mounted to the syringe 700. The syringe 700 includes a syringe outer tube 710 having a distal opening 711, a gasket 720 slidably provided inside the syringe outer tube 710, and a pusher 730 operated to move the gasket 720. The liquid 20 is stored in a space defined by the syringe outer tube 710 and the gasket 720. In addition, the injection needle 800 includes a needle body 820, and a hub 810 supporting the needle body 820. The injection needle 800 is mounted to the syringe 700 by fixing the hub 810 to the distal opening 711 by screw engagement, fitting or the like.

[2] Next, the needle body 820 of the syringe assembly 900 is made to pierce through the cap 4 of the medicine storage container 1, and a distal portion of the needle body 820 is located in the first space 21 of the container body 2. This results in that the inside of the syringe outer tube 710 and the inside of the container body 2 communicate with each other.

[3] Subsequently, in the state of [2] above, the pusher 730 of the syringe 700 is pushed in, whereby the liquid 20 is injected into the container body 2 through the needle body 820. The liquid 20 thus injected into the container body 2 is guided by the guide passages 6 to the inner surface 23*a* of the second space 23. The liquid 20 guided to the inner surface 23*a* of the second space 23 gradually flows down the inner surface 23*a*, and its flow velocity is suppressed by the gradually decreasing inside diameter zone 232, before it is supplied to the medicine 10 in a gentle manner. As a result, the medicine 10 is dissolved or dispersed in the liquid 20, and a liquid medicine 30 is obtained.

Thus, according to the medicine storage container 1, the liquid 20 can be gently supplied to the medicine 10, so that the foaming of the liquid medicine 30 is prevented. Therefore, the liquid medicine 30 which can be metered accurately and in which the medicine 10 is dissolved evenly can be obtained.

[4] Next, for example, the medicine storage container 1 is inverted upside down, thereby guiding the liquid medicine 30 through the guide passages 6 into the first space 21, and, in this state, the pusher 730 of the syringe 700 is moved toward the side opposite to the distal opening 711. By this the liquid medicine 30 can be sucked into the syringe outer tube 710. After the sucking-in of the liquid medicine 30 is over, the needle body 820 is pulled out from the cap 4.

A second embodiment representing another example of the medicine storage container disclosed here is described below with reference to FIGS. 3 and 4. The following description focuses primarily on differences between this embodiment of the medicine storage container and the first embodiment of the medicine storage container described above. Features in this second embodiment that are the same as features in the first embodiment are identified by common reference numerals and a detailed description of such features is not repeated.

The medicine storage container in this embodiment is the same as the medicine storage container in the first embodiment above, except for a difference in the configuration of the partition part.

Figure 3:
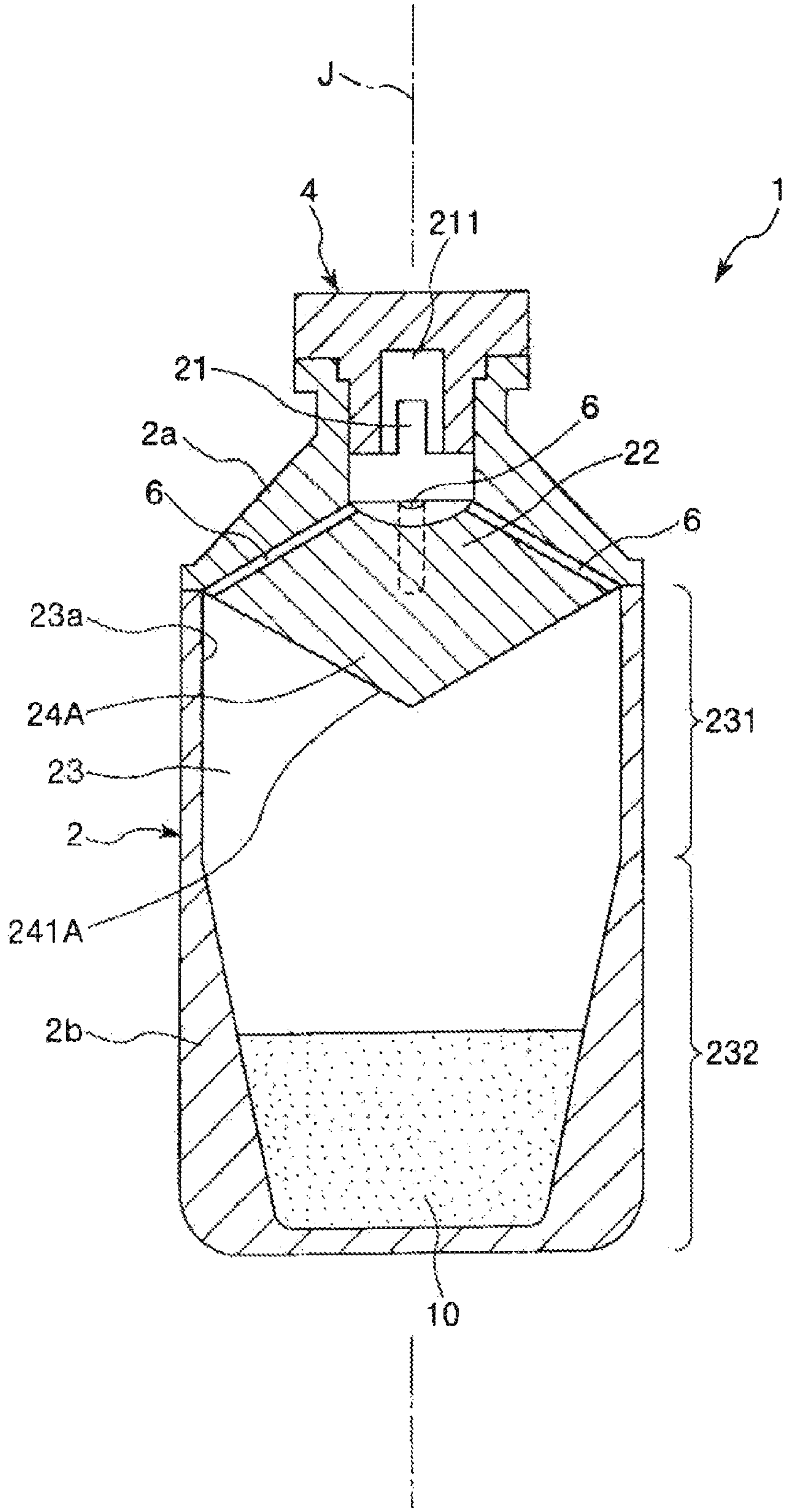
FIG. 3 is a longitudinal cross-sectional view showing a second embodiment of a medicine storage container disclosed here.

As shown in FIG. 3, a partition part 22 in this embodiment has a projected part 24*a* projected toward the inside of the second space 23. The projected part 24A is substantially conical in shape, and has an inclined surface 241A which is inclined inward along the direction toward the lower side of the container body 2. In addition, the inclined surface 241A is connected to that opening of each guide passage 6 which fronts on or opens to the second space 23. In other words, the opening of each guide passage 6 which fronts on or opens to the second space 23 is formed at a circumferential edge of the projected part 24A. With this projected part 24A provided, the following effect can be produced.

In sucking the liquid medicine 30 into the syringe outer tube 710 in the step [4] of the method of using the medicine storage container 1 as described in the first embodiment above, the sucking-in is conducted in the condition where the medicine storage container 1 is inverted upside down and the liquid medicine 30 is guided into the first space 21 through the guide passages 6. The projected part 24A as in the present embodiment helps ensure that when the medicine storage container 1 is inverted upside down, the liquid medicine 30 can be efficiently guided into the guide passages 6 owing to the inclination of the inclined surface 241A of the projected part 24A. Therefore, the liquid medicine 30 in the medicine storage container 1 can be used and recovered efficiently.

Figure 4:
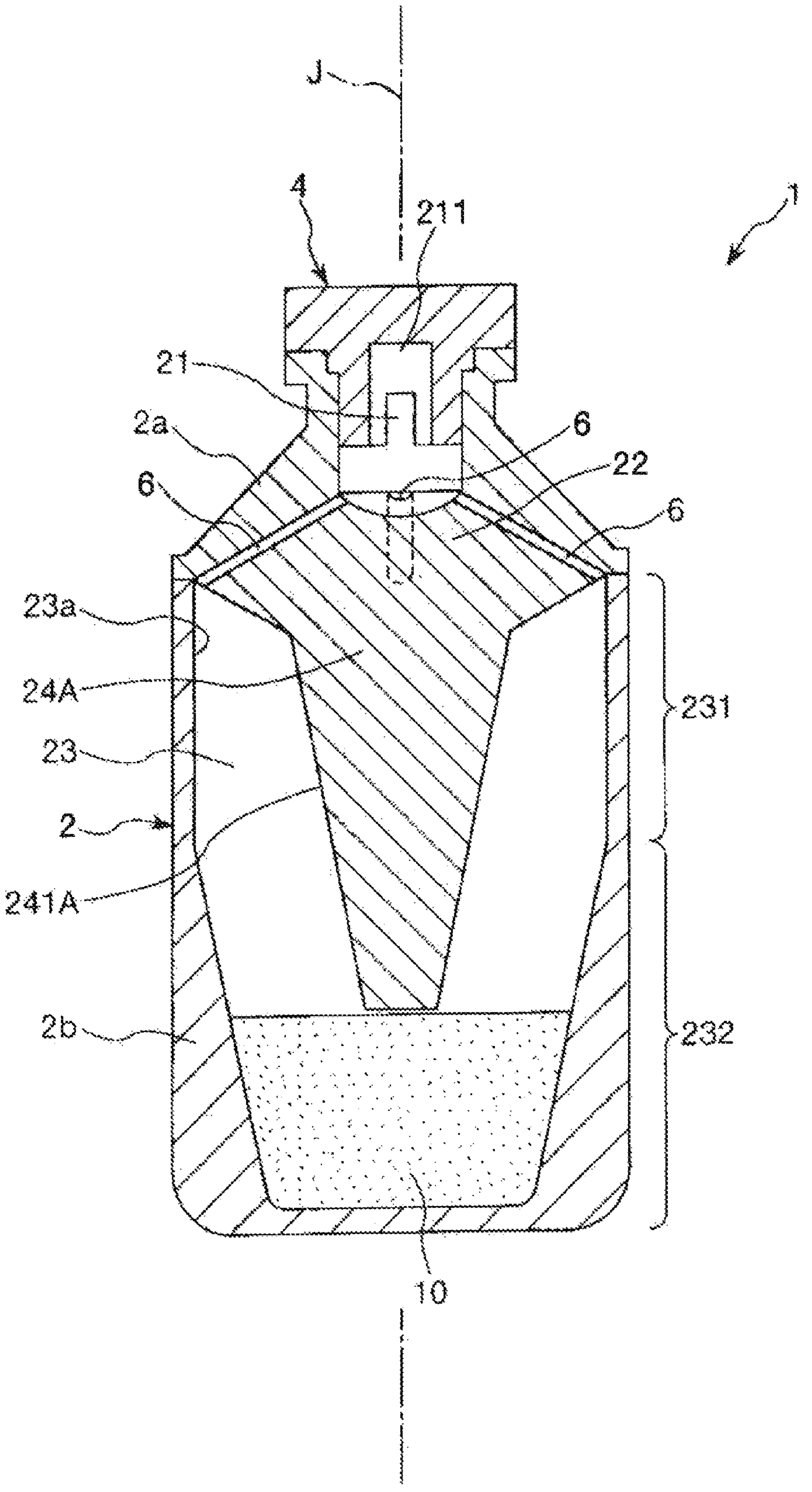
FIG. 4 is a longitudinal cross-sectional view showing a modification of the medicine storage container shown in FIG. 3.

In addition, as a modification of this embodiment, a configuration may be adopted in which, as shown in FIG. 4, a distal portion of the projected part 24A extends into the vicinity of the free surface of the medicine 10. Such a configuration helps ensure that even if the liquid 20 flows down the inclined surface 241A of the projected part 24A and drops off an apex portion of the projected part 24A down toward the medicine 10, the shock of the dropping can be reduced. Therefore, foaming of the liquid medicine 30 can be prevented more securely, while producing the above-mentioned effect. This effect is higher as the distance between the distal portion of the projected part 24A and the medicine 10 is smaller; further, this effect is maximized when the distal portion of the projected part 24A is in contact with the free surface of the medicine 10 or has penetrated into the medicine 10.

While the projected part 24A is so shaped that an inclination angle of the inclined surface 241A changes at an intermediate position in the configuration shown in FIG. 4, the shape of the projected part 24A is not restricted to this shape. The inclination angle of the inclined surface 241A may be constant or may be continuously varied.

A third embodiment representing another example of the medicine storage container disclosed here is described below with reference to FIG. 5. The following description focuses primarily on differences between this embodiment of the medicine storage container and the first embodiment of the medicine storage container described above. Features in this third embodiment that are the same as features in the first embodiment are identified by common reference numerals and a detailed description of such features is not repeated.

The medicine storage container according to this third embodiment is the same as the medicine storage container in the first embodiment above, except for a difference in the shape of each of the guide passages.

Figure 5:
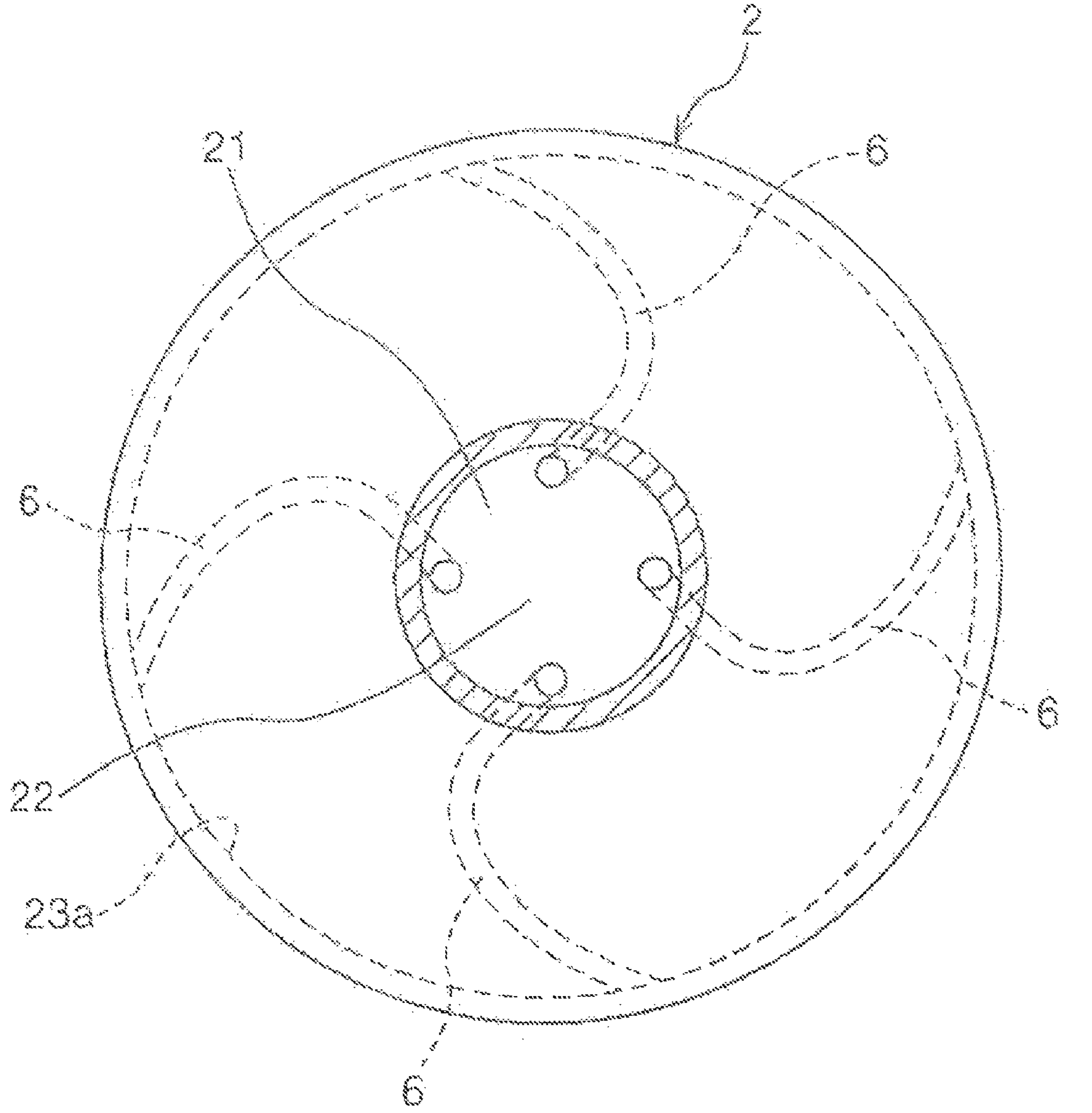
FIG. 5 is a cross-sectional view showing a third embodiment of a medicine storage container according to the disclosure here.

As shown in FIG. 5, each guide passage 6 in this embodiment is curved in a spiral shape in the circumferential direction of the container body 2. With each guide passage 6 formed in such a shape, a centrifugal force is exerted on the liquid 20 flowing within the guide passage 6, so that the liquid 20 guided to the inner surface 23*a* of the second space 23 spreads in a wetting manner into a wider range in the circumferential direction of the inner surface 23*a*. Therefore, the flow velocity of the liquid 20 flowing down the inner surface 23*a* can be suppressed, so that the liquid 20 can be supplied to the medicine 10 in a relatively gentle manner. In addition, since the liquid 20 can be supplied to the medicine 10 through the wider range, smooth mixing of the liquid 20 with the medicine 10 can be realized.

Figure 6:
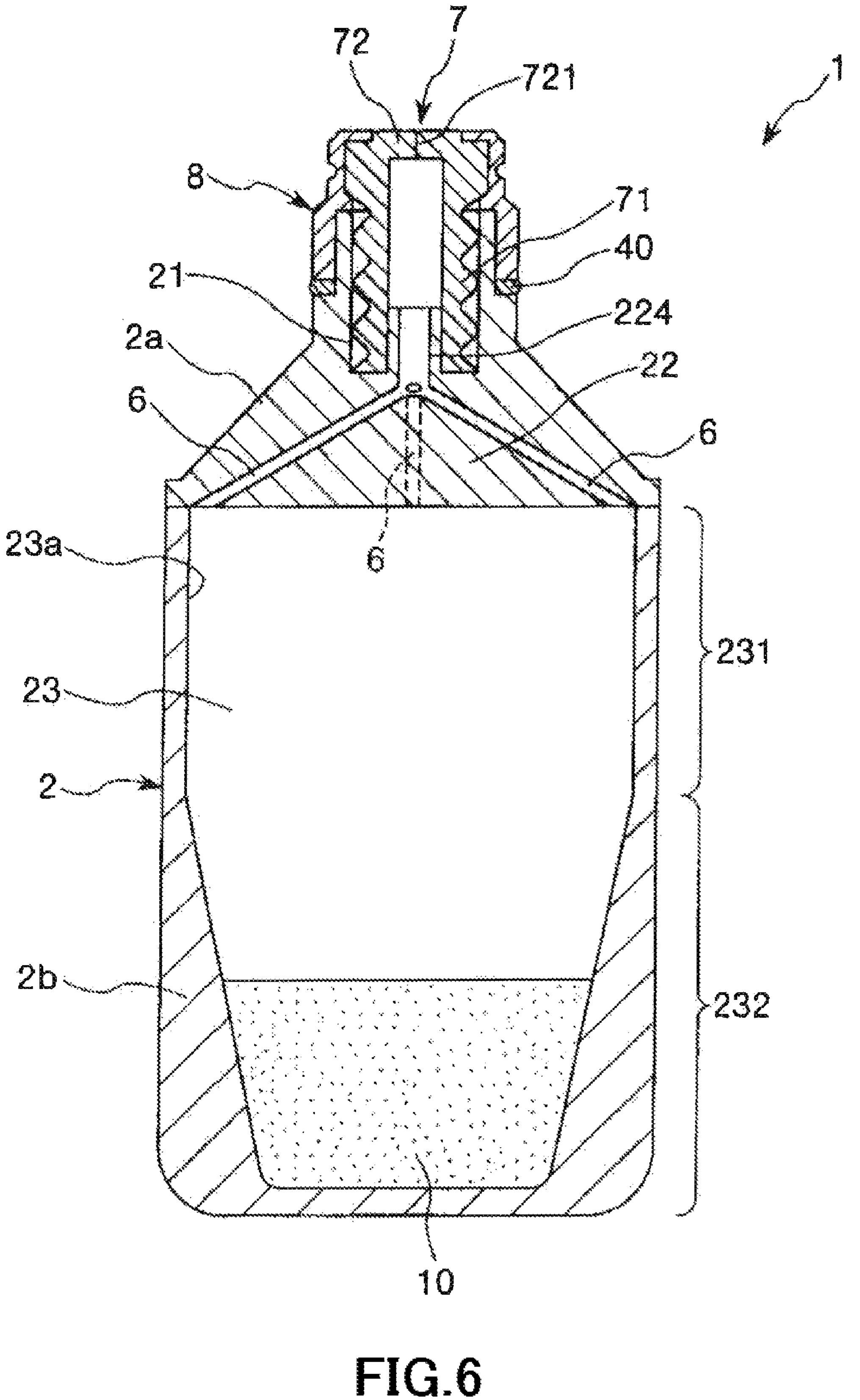
FIG. 6 is a longitudinal cross-sectional view showing a fourth embodiment of a medicine storage container disclosed here.

A fourth embodiment representing another example of the medicine storage container disclosed here is described below with reference to FIG. 6. The following description focuses primarily on differences between this embodiment of the medicine storage container and the first embodiment of the medicine storage container described above. Features in this fourth embodiment that are the same as features in the first embodiment are identified by common reference numerals and a detailed description of such features is not repeated.

The medicine storage container according to this fourth embodiment is the same as the medicine storage container in the first embodiment above, except for a difference in the configuration for maintaining the gas-tightness of the inside of the container body.

A container body 2 in this embodiment has a tube part 224 projecting from the partition part 22 into the first space 21. The tube part 224 communicates with each guide passage 6.

In addition, in the first space 21 of the container body 2, there are provided a valve 7 so provided as to shut off the opening 211, and a valve cap (fixing member) 8 for fixing the valve 7 to the container body 2. In this embodiment, gas-tightness of the inside of the container body 2 is maintained by this valve 7.

The valve 7 includes a tubular main body 71 in which the tube part 224 is positioned or inserted, and a valve part 72 which is provided at an upper end portion of the main body 71 and is so provided as to partition an inside and an outside of the main body 71 from each other. The valve 7 is entirely formed of an elastic material.

The material constituting the valve 7 is not specifically restricted. Examples of the material which can be used include elastic materials such as various rubber materials, for example, natural rubber, butyl rubber, isoprene rubber, butadiene rubber, styrene-butadiene rubber, silicone rubber, etc., various thermoplastic elastomers based on polyurethane, polyester, polyamide, olefin, styrene or the like, and their mixtures.

The valve part 72 is formed with an open-close port 721 which is opened when required. The open-close port 721 is composed of a slit, for example, a straight line-shaped slit, which is formed in a central portion of the valve part 72 so as to pierce through the valve part 72. When in a natural state, the valve part 72 is closed by elasticity of the valve part 72 in itself; on the other hand, when pressed in the axial direction by a distal portion of a syringe, for example, the valve part 72 is deformed to be opened.

Such a valve 7 is fixed to the container body 2 by putting its proximal end portion into the state of being inserted in the first space 21 and mounting the valve cap 8 to the container body 2. The valve cap 8 is fixed to the container body 2 by, for example, screw engagement or press fit. In a state in which the valve 7 is fixed to the container body 2, a proximal end face of the main body 71 is in gas-tight contact with a distal end face of the partition part 22, and the tube part 224 is inserted in the main body 71.

In addition, between the proximal end of the valve cap 8 and the container body 2, there is provided a seal member 40 for securing gas-tightness.

A method for using the medicine storage container 1 shown in FIG. 6 will be described, with the description focusing primarily on differences relative to the method associated with the first embodiment.

First, the syringe 700 with the liquid 20 stored therein is prepared. Next, the distal opening 711 of the syringe 700 is brought into contact with the valve part 72, and the valve part 72 is pressed in the direction toward the proximal end. As a result, the valve part 72 is deformed, and the open-close port is opened, whereby the inside of the syringe outer tube 710 and the first space 21 of the container body 2 communicate with each other. Thereafter, the medicine storage container 1 may be used in the same manner as in the first embodiment above.

A fourth embodiment representing another example of the medicine storage container disclosed here is described below with reference to FIGS. 7 and 8. The following description focuses primarily on differences between this embodiment of the medicine storage container and the first embodiment of the medicine storage container described above. Features in this fifth embodiment that are the same as features in the first embodiment are identified by common reference numerals and a detailed description of such features is not repeated.

The medicine storage container in this fifth embodiment is the same as the medicine storage container in the second embodiment above, except for a difference in the shape of the guide passages.

Figure 7:
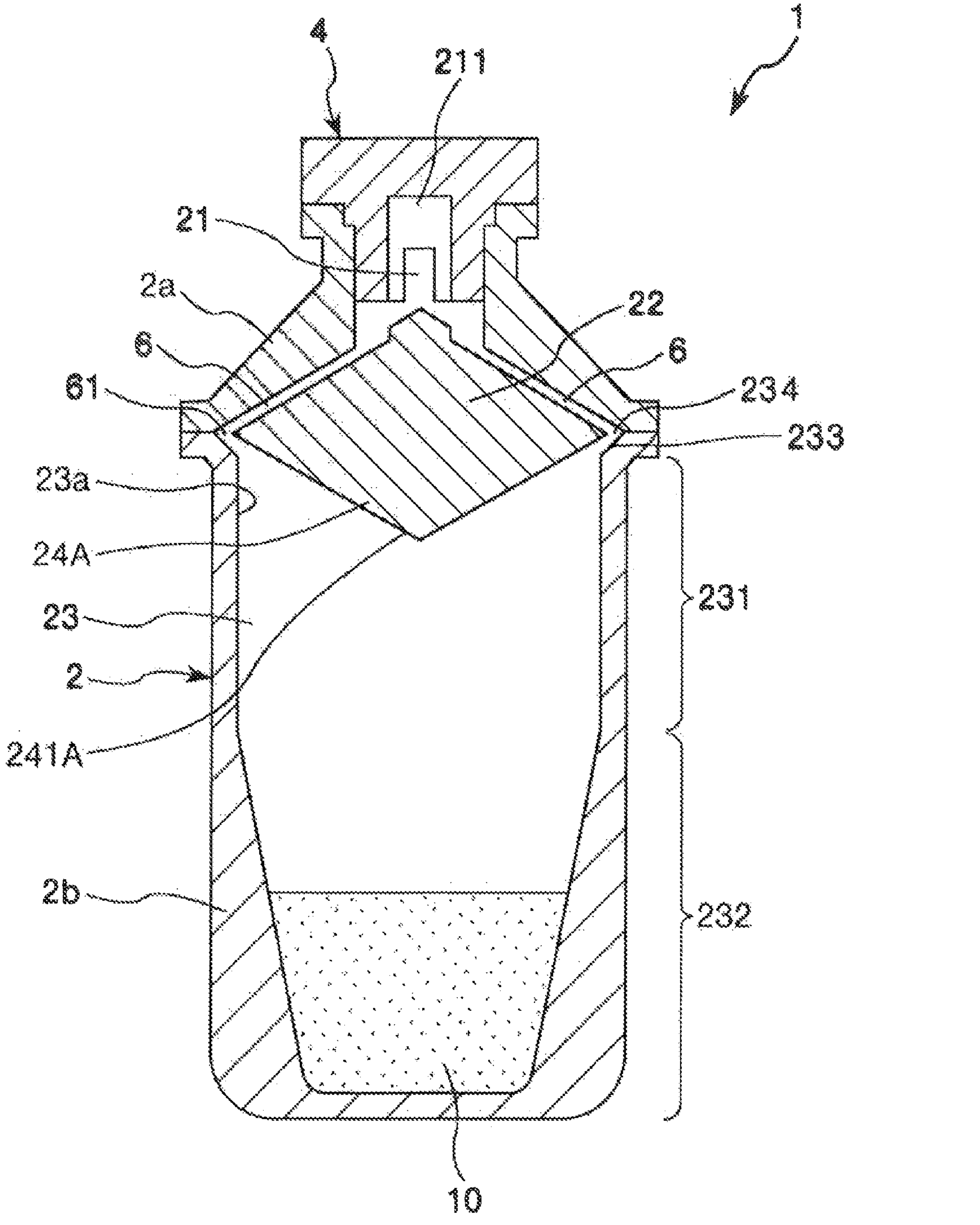
FIG. 7 is a longitudinal cross-sectional view showing a fifth embodiment of a medicine storage container disclosed here.
Figure 8:
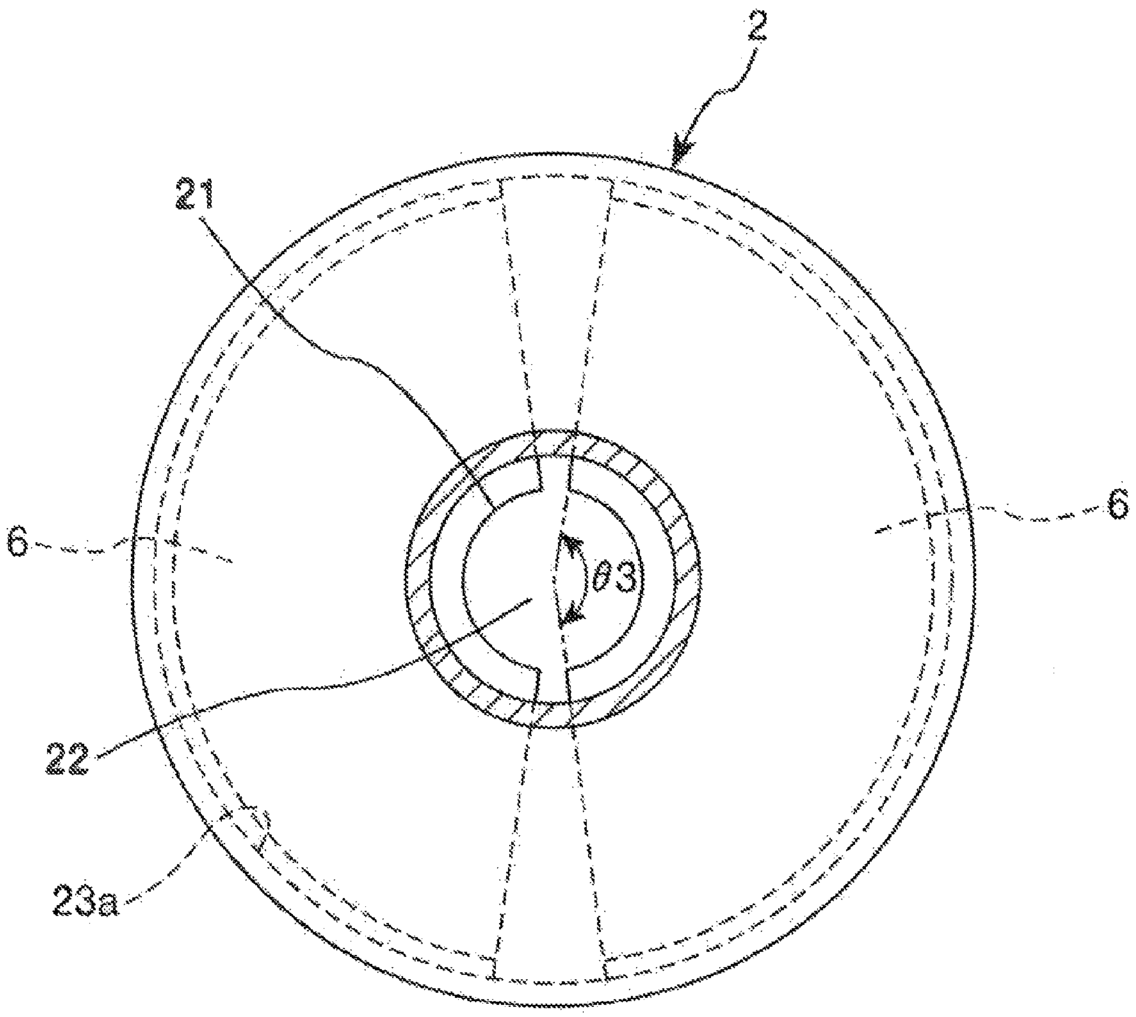
FIG. 8 is a cross-sectional view of the medicine storage container shown in FIG. 7.

As shown in FIG. 7, a partition part 22 is formed with a plurality (in this embodiment, two) of guide passages 6 through which the first space 21 and the second space 23 communicate with each other. Each of the guide passages 6 is formed along the inclination of the side surface of the partition part 22. In addition, as shown in FIG. 8, in a plan view of the medicine storage container 1 as viewed from above, each guide passage 6 is sector-shaped with a center on a center axis of the container body 2 being in a bottomed hollow cylinder-like shape, and the width of the guide passage 6 (the length in the circumferential direction of the partition part 22) gradually increased downstream in the flow direction of the liquid 20. The number of guide passages 6 is not restricted to two, but may be one or may be three or more.

In the plan view of the medicine storage container 1 as viewed from above, an angle 83 of the sector shape of each guide passage 6 is not particularly limited; preferably, it is about 150 to 175. In other words, a sum total of the angles 83 of the sector shapes of the guide passages is preferably about 300 to 350. This helps ensure that the liquid 20 guided to the inner surface 23*a* of the second space 23 through each guide passage 6 spreads into a wider range in the circumferential direction of the inner surface 23*a*. Consequently, the flow velocity of the liquid 20 flowing down the inner surface 23*a* can be suppressed. In addition, since the liquid 20 can be supplied to the medicine 10 through the wider range, smooth mixing of the liquid 20 with the medicine 10 can be achieved.

Furthermore, the liquid medicine 30 having the medicine 10 dissolved or dispersed in the liquid 20 can be smoothly recovered through the guide passages 6. When the medicine storage container 1 is inverted upside down in order to recover the liquid medicine 30, air in each of the guide passages 6 is swiftly moved into the second space 23. Therefore, it is possible to effectively lower the possibility of a situation in which the liquid medicine 30 to be recovered enrolls air when passing through the guide passages 6, with the result of foaming of the liquid medicine 30.

In addition, the inner surface 23*a* of the second space 23 adjacent to the guide passages 6 is formed with a tapered part (distal end gradually decreasing inside diameter part) 233. The inclination of the tapered part 233 is opposite to the inclinations of the guide passages 6, so that an angular part 234 is formed therebetween. Accordingly, the liquid 20 flowing through the guide passages 6 collides on the angular part 234. By flowing further along the tapered part 233, the flow velocity of the liquid 20 is lowered. Consequently, the flow velocity of the liquid 20 flowing down the inner surface 23*a* can be suppressed, and the liquid 20 can be gently supplied to the medicine 10. In addition, the liquid 20 having collided against the angular part 234 flows along the tapered part 233 rather assuredly, so that the liquid 20 can be guided to the inner surface 23*a* more assuredly.

While the medicine storage container according to the present invention has been described above by way of the embodiments shown in the drawings, the invention is not to be restricted to the embodiments. Each of the components of the medicine storage container can be replaced by components of arbitrary configurations which can show equivalent functions to those of the original ones. And additional structures may be added to the configurations in the embodiments.

In addition, the medicine storage container according to the present invention may be a combination of two or more configurations (characteristic features) selected from among the above-described embodiments.

According to the present invention, the dissolving liquid flows down the inner wall of the medicine storage container. Therefore, the dissolving liquid can be gently supplied to the medicine, particularly a protein preparation which is said to be susceptible to foaming, and the foaming of the liquid medicine can be restrained. Consequently, a liquid medicine which can be metered accurately and which contains a medicine dissolved uniformly can be obtained. Especially, with the inner wall of the medicine storage container inclined, the dissolving liquid can be supplied to the medicine more gently, whereby the above-mentioned effects are made more remarkable. Accordingly, the medicine storage container of the present invention has industrial applicability.

The detailed description above describes embodiments of a medicine storage container disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medicine storage container comprising:

a container body possessing a distal end and a proximal end, and in which a medicine is stored, the container body possessing a central axis which is orthogonal to a horizontal plane when the central axis is vertically oriented;

the container body including a first space on a side of the distal end and having an opening through which a liquid is injected, a second space storing the medicine, the second space provided closer to a side of the proximal end than the first space and possessing an inner surface;

a partition part spatially partitioning the first space and the second space;

the partition part including at least one guide passage communicating the first space and the second space and guiding the liquid injected through the opening into the first space to the inner surface of the second space;

the guide passage forming an angle other than 0° and other than 90° with the horizontal plane when the central axis is vertically oriented; and at least a center part of an upper surface of the partition part forming an angle other than 0° and other than 90° with the horizontal plane when the central axis is vertically oriented.

2. The medicine storage container according to claim 1, wherein the guide passage is so configured that the liquid guided to the inner surface is supplied to the medicine stored in the second space by flowing along the inner surface of the second space.

3. The medicine storage container according to claim 2, wherein:

the second space has a gradually decreasing inside diameter zone having an inside diameter gradually decreasing along a direction toward the side of the proximal end; and the liquid injected through the opening flows along an inner surface of the gradually decreasing inside diameter zone and is supplied to the medicine.

4. The medicine storage container according to claim 2, wherein the container body has a structure in which a first member constituting the first space and the partition part and a second member constituting the second space are joined to each other.

5. The medicine storage container according to claim 1, further comprising a valve or a cap configured to be pierced through by a needle body, the valve or the cap being provided at the opening to seal the container body in a gas-tight manner.

6. A medicine storage container comprising:

a hollow container body possessing a distal end and a proximal end;

the container body including a partition part, a first space and a second space;

the second space being located on a side of the partition part opposite the first space and being located closer toward the proximal end of the hollow container body than the first space, the second space containing medicine and possessing an inner surface surrounding the second space;

the first space being located on a side of the partition part opposite the second space and being located closer toward the distal end of the hollow container body than the second space, the first space having an opening through which liquid is injected to be mixed with the medicine in the second space;

the partition part spatially partitioning the first space from the second space;

the partition part including at least one guide passage having opposite open ends opening into the first space and the second space so that the first and second spaces are in fluid communication with one another through the at least one guide passage, the at least one guide passage being angled outwardly in a direction approaching the second space so that the liquid injected into the first space flows through the at least one guide passage and is guided toward the inner surface of the second space, enters the second space and flows down the inner surface of the second space; and a valve or a cap positioned so that the first space is located between the partition part and the valve or a cap, wherein the partition part possesses one end and an opposite end, the one end being located farther from the second space than the opposite end, the partition part possessing an outer diameter that increases from the one end toward the opposite end.

7. The medicine storage container according to claim 6, wherein the at least the one guide passage includes a plurality of guide passages, and the plurality of guide passages are provided at circumferentially spaced intervals of the partition part.

8. The medicine storage container according to claim 6, wherein the container body comprises a first member constituting the first space and the partition part, and a second member constituting the second space, with the first and second members being joined to each other.

9. The medicine storage container according to claim 6, wherein the valve or the cap is a valve positioned in the first space of the container body.

10. The medicine storage container according to claim 6, further comprising a valve cap fixing the valve to the container body.

11. The medicine storage container according to claim 2, wherein the container body possesses an inner circumferential surface surrounding the second space, and the guide passage possesses a proximal end that opens at the inner circumferential surface at a distal end of the second space.

12. The medicine storage container according to claim 1, wherein the partition part possesses one end and an opposite end, the one end being located farther from the second space than the opposite end, the partition part possessing an outer diameter that increases from the one end toward the opposite end.

13. The medicine storage container according to claim 1, wherein the partition part is truncated cone-shaped.

14. The medicine storage container according to claim 1, wherein the partition part possesses a top face that is cone-shaped.

15. The medicine storage container according to claim 1, further comprising at least one additional guide passage provided at a circumferentially spaced interval of the partition part.

16. The medicine storage container according to claim 6, wherein the guide passage is so configured that the liquid guided to the inner surface is supplied to the medicine stored in the second space by flowing along the inner surface of the second space.

17. The medicine storage container according to claim 6, wherein the container body possesses an inner circumferential surface surrounding the second space, and the guide passage possesses a proximal end that opens at the inner circumferential surface at a distal end of the second space.

18. A medicine storage container comprising:

a container body possessing a distal end and a proximal end, and in which a medicine is stored, the container body possessing a central axis which is orthogonal to a horizontal plane when the central axis is vertically oriented;

the container body including a first space on a side of the distal end and having an opening through which a liquid is injected, a second space storing the medicine, the second space provided closer to a side of the proximal end than the first space and possessing an inner surface;

a partition part spatially partitioning the first space and the second space;

the partition part including at least one guide passage communicating the first space and the second space and guiding the liquid injected through the opening into the first space to the inner surface of the second space;

the guide passage forming an angle other than 0° and other than 90° with the horizontal plane when the central axis is vertically oriented; and at least a center part of an upper surface of the partition part forming an angle other than 0° and other than 90° with the horizontal plane when the central axis is vertically oriented, wherein the container body possesses an inner circumferential surface surrounding the second space, and the guide passage possesses a proximal end that opens at the inner circumferential surface at a distal end of the second space.

19. The medicine storage container according to claim 18, wherein the partition part possesses one end and an opposite end, the one end being located farther from the second space than the opposite end, the partition part possessing an outer diameter that increases from the one end toward the opposite end.

20. The medicine storage container according to claim 18, further comprising at least one additional guide passage provided at a circumferentially spaced interval of the partition part.

* * * * *